United States Patent [19]

Todd et al.

[11] Patent Number: 5,423,745
[45] Date of Patent: Jun. 13, 1995

[54] IRREGULAR SURFACE BALLOON CATHETERS FOR BODY PASSAGEWAYS AND METHODS OF USE

[75] Inventors: Robert J. Todd; Gary L. Crocker, both of Salt Lake City, Utah

[73] Assignee: Research Medical, Inc., Salt Lake City, Utah

[21] Appl. No.: 271,261

[22] Filed: Jul. 6, 1994

Related U.S. Application Data

[63] Continuation of Ser. No. 967,164, Oct. 27, 1992, abandoned, which is a continuation-in-part of Ser. No. 710,809, Jun. 4, 1991, abandoned, which is a continuation-in-part of Ser. No. 187,230, Apr. 28, 1988, Pat. No. 5,021,045.

[51] Int. Cl.$^6$ ............................................. A61M 25/00
[52] U.S. Cl. ......................................... 604/53; 604/96
[58] Field of Search ..................... 604/53, 96, 102–103, 604/280–281; 606/192, 194

[56] References Cited

U.S. PATENT DOCUMENTS

| | | | |
|---|---|---|---|
| 1,049,087 | 12/1912 | Hill | 36/59 C |
| 1,060,665 | 5/1913 | Bell | 604/281 |
| 1,190,179 | 7/1916 | Livingston | 4/583 |
| 1,282,881 | 10/1918 | Landis . | |
| 1,289,106 | 12/1918 | Bullock | 36/59 C |
| 2,164,926 | 7/1939 | Kleine | 604/170 |
| 2,538,215 | 1/1951 | Stack | 128/227 |
| 2,669,233 | 2/1954 | Friend | 128/251 |
| 2,701,559 | 2/1955 | Cooper | 128/756 |
| 2,927,584 | 3/1960 | Wallace . | |
| 2,983,512 | 5/1961 | Fleischer | 273/81 R |
| 3,635,223 | 1/1972 | Klieman | 606/194 |
| 3,678,959 | 7/1972 | Liposky | 137/625.11 |
| 3,726,269 | 4/1973 | Webster, Jr. | 128/2.05 F |
| 3,766,924 | 10/1973 | Pidgeon | 128/325 |
| 3,813,729 | 6/1974 | Szabo et al. | 273/75 |
| 3,815,608 | 6/1974 | Spinosa et al. . | |
| 3,859,985 | 1/1975 | Eckhart | 128/2.05 R |
| 3,970,090 | 7/1976 | Loiacono . | |
| 4,154,227 | 5/1979 | Krause et al. | 128/1 D |
| 4,210,478 | 7/1980 | Shoney | 156/242 |
| 4,249,923 | 2/1981 | Walda | 62/394 |
| 4,284,073 | 8/1981 | Krause et al. | 128/1 D |
| 4,290,428 | 9/1981 | Durand et al. | 604/97 |
| 4,351,341 | 9/1982 | Goldberg et al. | 128/348 |

(List continued on next page.)

FOREIGN PATENT DOCUMENTS

| | | | |
|---|---|---|---|
| 451133 | 9/1948 | Canada | 273/81 R |
| 249338 | 12/1987 | European Pat. Off. | 604/53 |
| 1249338 | 12/1987 | European Pat. Off. | A61M 25/00 |
| 873041982 | 12/1987 | European Pat. Off. | A61M 25/00 |

OTHER PUBLICATIONS

USCI Catalog, 1967–68, p. 41.
ACMI Catalog, Apr. 1972, p. 18, Pelham NY.
Gerald D. Buckberg, M.D., "Reterograde Pulmonary Venous Pressure Measurement–Fact or Artifact?", The Journal of Thoracic and Cardiovascular Surgery, vol. 59, No. 3, pp. 393–406, Mar. 1970.
(List continued on next page.)

*Primary Examiner*—Stephen C. Pellegrino
*Assistant Examiner*—Nancy Mulcare
*Attorney, Agent, or Firm*—Workman, Nydegger & Seeley

[57] ABSTRACT

This invention relates to balloon catheters for use in infusing a solution into a body passageway, and their methods of use and manufacture. Each catheter contains at least one lumen through which a solution flows into the body. The balloons of each catheter are secured to the proximal end of the catheter, and each have a plurality of protuberances projecting outwardly from the outer surface of the balloons for the purpose of firmly gripping the walls of the body passageway so as to secure placement of the catheter within the passageway. A malleable wire assists in retaining the catheter in position within the body passageway. A double balloon catheter allows sealing of the body passageway to be accomplished separately from securely gripping the walls.

20 Claims, 7 Drawing Sheets

U.S. PATENT DOCUMENTS

| | | | |
|---|---|---|---|
| 4,397,335 | 8/1983 | Doblar et al. | 137/625.19 |
| 4,413,989 | 11/1983 | Schjeldahl et al. | 604/96 |
| 4,416,280 | 11/1983 | Carpenter et al. | 128/399 |
| 4,427,009 | 1/1984 | Wells et al. | 128/400 |
| 4,433,971 | 2/1984 | Lindsay et al. | 604/122 |
| 4,447,590 | 5/1984 | Szycher | 528/76 |
| 4,459,977 | 7/1984 | Pizon et al. | 128/1 D |
| 4,465,072 | 8/1984 | Taheri . | |
| 4,493,697 | 1/1985 | Krause et al. | 604/50 |
| 4,512,163 | 4/1985 | Wells et al. | 62/394 |
| 4,512,762 | 4/1985 | Spears | 604/21 |
| 4,529,397 | 7/1985 | Hennemuth et al. | 604/4 |
| 4,531,935 | 7/1985 | Berryessa | 604/45 |
| 4,531,936 | 7/1985 | Gordon | 604/49 |
| 4,535,757 | 8/1985 | Webster, Jr. | 128/1 D |
| 4,566,480 | 1/1986 | Parham | 137/271 |
| 4,568,330 | 2/1986 | Kujawaski et al. | 604/53 |
| 4,610,661 | 9/1986 | Possis et al. | 604/52 |
| 4,648,384 | 3/1987 | Schmukler | 128/1 D |
| 4,668,215 | 5/1987 | Allgood | 604/30 |
| 4,689,041 | 8/1987 | Corday et al. | 604/53 |
| 4,714,460 | 12/1987 | Calderon | 604/28 |
| 4,721,109 | 1/1988 | Healey . | |
| 4,753,637 | 6/1988 | Horneffer | 604/53 |
| 4,762,130 | 8/1988 | Fogarty et al. | 606/194 |
| 4,784,638 | 11/1988 | Ghajar et al. | 604/280 |
| 4,804,358 | 2/1989 | Karcher et al. | 600/17 |
| 4,850,969 | 7/1989 | Jackson | 604/96 |
| 4,927,412 | 5/1990 | Menasche | 606/192 |
| 4,927,412 | 5/1990 | Menasche | 604/96 |
| 4,931,330 | 6/1990 | Stier et al. | 4/582 |
| 4,957,485 | 9/1990 | Andersson et al. | 604/96 |
| 5,021,045 | 6/1991 | Buckberg et al. | 604/96 |
| 5,024,668 | 6/1991 | Peters et al. | 606/194 |
| 5,041,093 | 8/1991 | Chu | 604/104 |
| 5,158,545 | 10/1992 | Trudell et al. | 604/53 |
| 5,173,346 | 12/1992 | Middleton | 4/582 |
| 5,180,368 | 1/1993 | Garrison | 604/104 |
| 5,197,952 | 3/1993 | Marcadis et al. | 604/96 |
| 5,295,994 | 3/1994 | Bonutti | 606/192 |

OTHER PUBLICATIONS

Philippe Menasche, M.D., et al., "Retrograde Coronary Sinus Perfusion: A Safe Alternative for Ensuring Cardioplegic Delivery in Aortic Valve Surgery", The Annals of Thoracic Surgery, Vo. 34, No. 6, Dec. 1982, pp. 647–658.

Gerald D. Buckberg, M.D., "Strategies and Logic of Cardioplegic Delivery to Prevent, Avoid, and Reverse Ischemic and Reperfusion Damage", The Journal of Thoracic and Cardiovascular Surger, 1987; vol. 93, pp. 127–139.

Donald G. Mulder et al., "Myocardial Protection During Aortic Valve Replacement", The Annals of Thoracic Surgery, vol. 21, No. 2, Feb. 1976, pp. 123–130.

Jorge Solorzano, M.D. et al., "Retrograde C oronary Sinus Perfusion for Myocardial Protection During Cardiopulmonary Bypass", The Annals of Thoracic Surgery, vol. 25, No. 3, Mar. 1978, pp. 201–208.

Philippe Menasche et al., "Retrograde Coronary Sinus Perfusion", Roberts Textbook Myocardial Protection in Cardiac Surgery, printed 1987, Chapter 15, pp. 251–262.

Charles C. Reed, Diane K. Clark, Chapter 19, "Cannulation", Chapter 23 Myocardial Protection, Cardiopulmonary Perfusion, Texas Medical Press, Inc., Houston, Tex., 1975.

Dr. Dwight C. McGoon, "Coronary Perfusion", Journal of Thoracic and Cardiovascular Surgery, vol., 70, No. 6, p. 1025, Dec. 1975.

International Working Group on Coronary Sinus Interventions, Newsletter, vol. 1, No. 3, Oct., 1987.

Gerald D. Buckberg, M.D., "Retrograde Pulmonary Venous Pressure Measurement–Fact or Artifact?", *The Journal of Thoracic and Cardiovascular Surgery*, vol. 59, No. 3, pp. 393–406, Mar. 1970.

Gerald D. Buckberg, M.D., "Strategies and Logic of Cardioplegic Delivery to Prevent, Avoid, and Reverse Ischemic and Reperfusion Damage", *The Journal of Thoracic and Cardiovascular Surgery*, 1987, vol. 93, pp. 127–139.

Richard M. Engelman, M.D., "Retrograde Continuous Warm Blood Cardioplegia", Ann Thorac Surg, 1991, vol. 51, pp. 180–181.

John W. Kirklin, M.D., et al., "Prevention of Myocardial Damage During Cardiac Operations", *The New England Journal of Medicine*, Jul. 1979, vol. 301, No. 3, pp. 135–141.

Dwight C. McGoon, M.D., "Coronary Perfusion", *Journal of Thoracic and Cardiovascular Surgery*, vol. 70, No. 6, p. 1025, Dec. 1975.

Philippe Menasche, et al., "Retrograde Coronary Sinus Perfusion", Roberts Textbook Myocardial Protection in (List continued on next page.)

OTHER PUBLICATIONS

*Cardiac Surgery,* printed 1987, Chapter 15, pp. 251–262.

Philippe Menasche, M.D., et al., "Retrograde Coronary Sinus Perfusion: A Safe Alternative for Ensuring Cardioplegic Delivery in Aortic Valve Surgery", *The Annals of Thoracic Surgery,* vol. 34, No. 6, Dec. 1982, pp. 647–658.

Donald G. Mulder, et al., "Myocardial Protection During Aortic Valve Replacement", *The Annals of Thoracic Surgery,* vol. 21, No. 2, Feb. 1976, pp. 123–130.

D. Glenn Pennington, "Direct Coronary Ostial Perfusion", *Nyocardial Protection in Cardiac Surgery,* edited by Arthur J. Roberts, published by Marcel Dekker Corp., New York and Basel, 1067; pp. 229–250.

Charles C. Reed, Diane K. Clark, Chapter 19, "Cannulation", Chapter 23 Myocardial Protection, *Cardiopulmonary Perfusion,* Texas Medical Press, Inc., Houston, Tex., 1975.

Tomas A. Salerno, M.D., "Retrograde Continuous Warm Blood Cardioplegia: A New Concept in Myocardial Protection", *Ann Thorac Surg,* 1991, vol. 51, pp. 245–247.

Jorge Solorzano, M.D., et al., "Retrograde Coronary Sinus Perfusion for Myocardial Protection During Cardiopulmonary Bypass", *The Annals of Thoracic Surgery,* vol. 25, No. 3, Mar. 1978, pp. 201.–208.

International Working Group on Coronary Sinus Interventions, Newsletter, vol. 1, No. 3, Oct., 1987.

S. F. Bolling, M.D. et al., *"Improved Myocardial Preservation During Global Ischemia by Continuous Retrograde Coronary Sinus Perfusion,"* Thoracic and Cardiovascular Surgery, No. 5, pp. 659–666 (Nov., 1983).

N. E. Shumway, M.D., *"Forward Versus Retrograde Coronary Perfusion for Direct Vision Surgery of Acquired Aortic Valvular Disease,"* J. Thoracic and Cardiovas. Surg., vol. 38, No. 1, pp. 75–80 (Jul. 1959).

J. C. Farcot et al., "[New Catheter–Pump System for Diastolic Synchronized Coronary Sinus Retroperfusion," Medical Progress Through Technology, pp. 29–37 (1980).

B. J. King, M.B., B. Chir., *"An Improved Coronary Artery Perfusion Cannula,"* J. Thoracic and Cardiovas. Sur., pp. 667–668.

J. C. Farcot et al., *"New Catheter–Pump System for Diastolic Synchronized Coronary Sinus Retroperfusion (D.S.R.),"* pp. 367–374.

IRREGULAR SURFACE BALLOON CATHETERS FOR BODY PASSAGEWAYS AND METHODS OF USE

RELATED APPLICATION

This application is a continuation of prior application Ser. No. 07/967,164, filed on Oct. 27, 1992, now abandoned, which is a continuation-in-part of Ser. No. 07/710,809 filed Jun. 4, 1991, now abandoned, which is a continuation-in-part of Ser. No. 07/187,230 filed Apr. 28, 1988, U.S. Pat. No. 5,021,045.

THE FIELD OF THE INVENTION

The present invention is directed to balloon catheters and the methods of their use and manufacture. More particularly, the present invention is directed to the specific features and structures of balloons used in balloon catheters.

BACKGROUND OF THE INVENTION

It is often necessary in medical procedures to be able to transport materials between body passageways and external areas in a secure and accurate manner. Typically, a catheter is inserted into a body passageway and a solution is either infused into the body from an external source, or fluid is drained out of the body to an external location.

Many types of balloon catheters are available for these procedures. For drainage of fluid from a body passageway, a single lumen catheter may be sufficient. For infusion, catheters may be provided with additional lumens for such functions as temperature or pressure sensing, or for infusing more than one fluid at the same time without mixing prior to infusion. In some cases, a single catheter having multiple lumens is useful for simultaneous drainage and infusion.

In many of these procedures, proper placement of the catheter within the body passageway is important to the safety of the patient and success of the procedure. In some cases, a precise placement of the catheter is necessary throughout the procedure. Yet, movement in the region where the catheter is located sometimes causes the catheter to be dislodged from its original position within the passageway. As a result, the smooth flow of fluid into or out of the body can be disrupted or can be directed to or from an improper location. In addition, movement of a catheter within a body passageway may also cause damage to surrounding tissues.

It will be appreciated that a seal must be formed between the catheter and the body passageway for the procedures to be completely successful. For example, when infusing fluids, such infusion is performed under pressure to obtain a desired result. Failure to effect a seal at the location of the balloon results in leakage, and concomitant failure to maintain the desired pressure within the body passageway.

The development of balloon catheters has increased the security of catheter placement within body passageways. These catheters employ a balloon, located at the distal end of the catheter, that, when inflated, wedges the catheter in place as the balloon engages the walls of the body passageway. The inflated balloon may also form the necessary seal between the inflated balloon and the body passageway.

Many different types of balloon catheters are in use today. For example, the balloon may be a manually inflatable balloon, wherein a special lumen in communication therewith is usually provided for inflation and deflation of the balloon. Air or fluid is passed through the special lumen into the balloon to cause inflation of the balloon, and is drained out of the balloon to cause deflation. When inflated, the balloon assists in retaining the catheter in place. When the user wishes to remove the catheter, he or she simply removes the air or fluid from the balloon until the balloon is deflated. The catheter may then be easily removed.

One example of a manually inflatable balloon catheter in use today is disclosed in U.S. Pat. No. 4,689,041 issued to Corday. Corday discloses a balloon catheter having a hollow secondary tube in fluid communication with the interior of the balloon. The secondary tube allows for inflation and deflation of the balloon.

Another manually inflatable balloon catheter is disclosed by U.S. Pat. No. 4,648,384 issued to Schmukler. In Schmukler, a pump is used to pump gas through an extra lumen into the balloon in order to inflate the balloon. For deflation, the gas is released.

A second type of balloon catheter employs a self-inflating balloon. This balloon is typically in direct communication with the main lumen through apertures on the lumen which open into the balloon. A solution flowing through the lumen would enter the balloon and cause inflation. Stopping the flow of the fluid would cause the balloon to drain and inflate.

One example of this type of catheter is disclosed in a European Patent No. 249,338 issued to Spector et al., wherein the balloon is inflated and deflated by flow of arterial blood through the main lumen. Another example is disclosed by U.S. Pat. No. 5,021,045 issued to Buckberg et al.

In the past, people have attempted to secure balloon catheters in place by raising the pressure within the balloon so that the balloon expands more tightly against surrounding tissues. Unfortunately, high pressures can cause damage to the tissues as the tissues themselves are stretched due to the pressure of the expanding balloon. In cases where the tissue being treated is already damaged or diseased, high pressures can aggravate the damaged tissues.

Cardiac surgery is one area where rapid, safe, and secure infusion of solution into the body is necessary. Since the early days of cardiac surgery, it has been recognized that in order to provide the optimum surgical conditions when operating on the heart, it is necessary to interrupt the normal operation of the heart. For obvious reasons, an arrested, flaccid heart is preferred during a cardiac surgical procedure over a beating heart with blood flowing through it. Thus, in order to be able to efficiently perform cardiac surgery, it is often necessary to use cardiopulmonary-bypass techniques and to isolate the heart from its life-giving blood supply.

The normal heart receives its blood supply through the left and right coronary arteries which branch directly from the aorta. Generally, the veins draining the heart flow into the coronary sinus which empties directly into the right atrium. A few veins, known as thesbian veins, open directly into the atria or ventricles of the heart.

The most recent method developed utilizes continuous warm blood cardioplegia. Warm oxygenated blood cardioplegia has certain theoretical advantages over cold cardioplegia, such as continuously supplying oxygen and substrates to the arrested heart while avoiding the side effects of hypothermia. Salerno, Thomas A. et al., "Retrograde Continuous Warm Blood Cardioplegia: A New Concept in Myocardial Protection" 51 *Annual of Thoracic Surgery* 245 (1991).

The use of warm blood cardioplegia to protect the myocardium has proven the most advantageous method of those used to date. Cardioplegia, which literally means "heart stop," may be administered in an antegrade manner (through arteries in the normal direction of blood flow), in a retrograde manner (through veins opposite the normal blood flow direction), or in a combination of retrograde and antegrade administration. Cardioplegic solutions, typically containing potassium, magnesium procaine, or a hypocalcemic solution, stop the heart by depolarizing cell membranes.

Warm-blood cardioplegia is often initiated by placing an aortic antegrade cardioplegia cannula followed by the placement of a retrograde coronary sinus catheter. A high-potassium (20–30 mEq KCl liter) warm blood cardioplegic solution is infused through the antegrade cannula to rapidly induce arrest. Following diastolic arrest, perfusion is switched to a low-potassium (8–10 mEq KCl liter) solution infused continuously through the retrograde coronary sinus catheter at an infusion pressure at the cannula tip of less than 40 mm Hg.

While warm-blood cardioplegia has some advantages over prior methods, one problem encountered in the retrograde administration of warm-blood cardioplegia occurs in the placement of the retrograde coronary sinus catheter. A normothermic coronary sinus is more distensible and dilated than a corresponding hypothermic coronary sinus. As a result, placement of the retrograde catheter is difficult to maintain. Catheters designed for use in hypothermic conditions become flaccid and do not retain the shape necessary to maintain proper positioning of the catheter.

The development of retrograde coronary sinus catheters with self-inflating balloons has increased the security of catheter placement. These catheters employ a balloon, located at the distal end of the catheter, that inflates as cardioplegic solution is infused through the catheter. The inflation of the balloon in the coronary sinus wedges the retrograde catheter in place as the balloon engages the walls of the coronary sinus.

While engagement of the walls of the coronary sinus serves to secure the retrograde catheter in place during hypothermic cardioplegia (when the walls of the coronary sinus are relatively less distensible and dilated), the inflatable balloons designed for hypothermic cardioplegia do not necessarily function well in a normothermic environment.

The increased distensibility and size of a normothermic coronary sinus relative to a hypothermic coronary sinus prevents the inflatable balloon from securing an adequate purchase upon the walls of the coronary sinus. Pressure from the inflatable balloon against the walls of the coronary sinus merely dilates the warm coronary sinus farther, resulting in slippage and displacement of the retrograde catheter within the coronary sinus.

Clearly, this is a potentially dangerous situation, and in any event degrades the effectiveness of the procedure. Although slippage and displacement is carefully monitored, it has continued to be a problem and a serious concern.

BRIEF SUMMARY AND OBJECTS OF THE INVENTION

The present invention is directed to balloon catheters and the methods of their use. The balloon catheters of the present invention are designed for secure placement and sealing within body passageways. A particularly useful application for the balloon catheters of the present invention is in connection with the infusion of cardioplegia solutions.

The balloon catheter of the present invention is used to transport a fluid between a body passageway and an external location (either drainage or infusion). The catheter includes a flexible cannula having at least one lumen with a distal end being of a size capable of insertion into a body passageway, and a proximal end capable of connection to an outside location.

A balloon is secured to the cannula periphery near the distal end of the catheter. This balloon forms a chamber within the balloon and the outside of the cannula. Gripping means for securely gripping the walls of a body passageway in order to secure the catheter in place within the passageway, project outwardly from the outer surface of the balloon. When the balloon is inflated, the gripping means come into contact with the walls of the body passageway. Although the balloon must be inflated with enough pressure to form a seal, it has been found that the pressure necessary in a balloon provided with gripping means in accordance with the present invention is less than required in a conventional balloon.

Expansion means for inflating the balloon are located on the catheter in communication with the balloon. When the balloon is a self-inflating balloon, the expansion means may comprise at least one aperture in the lumen which opens into the chamber of the balloon. These apertures allow the solution to fill and inflate the balloon while the solution is flowing. When the flow of the solution stops, the balloon loses its turgidity. Additionally, as a solution flows through the lumen of the catheter of the present invention, the self-inflating balloon fills to seal the body passageway. Protuberances on the balloon's outer surface assist in gripping the walls of the body passageway such that the catheter is held firmly within the walls.

When the balloon is the manually inflatable type, the expansion means may be a lumen which opens into the balloon, and which is separate from the main lumen through which the fluid to be transported flows. Gas or liquid flowed through the separate lumen inflates the balloon.

A malleable wire is optionally incorporated into the catheter to assist in the retention of the shape of the catheter after installation. The malleable wire gives the catheter additional rigidity particularly useful when using warm solutions such as cardioplegic solutions.

It is, therefore, an object of the present invention to provide a balloon catheter for transporting a solution between a body passageway and an external location which can be positioned securely within the body passageway during drainage or infusion of the solution.

Another object of the present invention is to provide a balloon catheter having therein a malleable wire that has sufficient rigidity to sustain the shape of the catheter under normothermic conditions.

Yet another object of the present invention is to provide a balloon catheter that can grip the walls of the body passageway during normothermic conditions so as to firmly secure the catheter within the walls of the body passageway.

Still another object of the present invention is to provide a balloon catheter that can grip the walls of the body passageway securely and form a seal with the passageway without causing undue damage to the tissues.

These and other objects and features of the present invention will become more fully apparent from the following description and appended claims taken in conjunction with the accompanying drawings.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict the best mode presently contemplated for the practice of the present invention, nevertheless, they are merely exemplary embodiments of the invention and are not therefore to be considered limiting of its scope. In the accompanying drawings.

DETAILED DESCRIPTION OF THE PREFERRED EMBODIMENTS

A. The Balloon catheter

The present invention relates to balloon catheters for use in transporting a fluid between a body passageway and an external location. Such catheters are held securely in place by the inventive balloons of the present invention. These balloons can be used with many different types of catheters for insertion into different body passageways in order to infuse a liquid into, or drain a liquid from, the body passageway.

Figure 1:
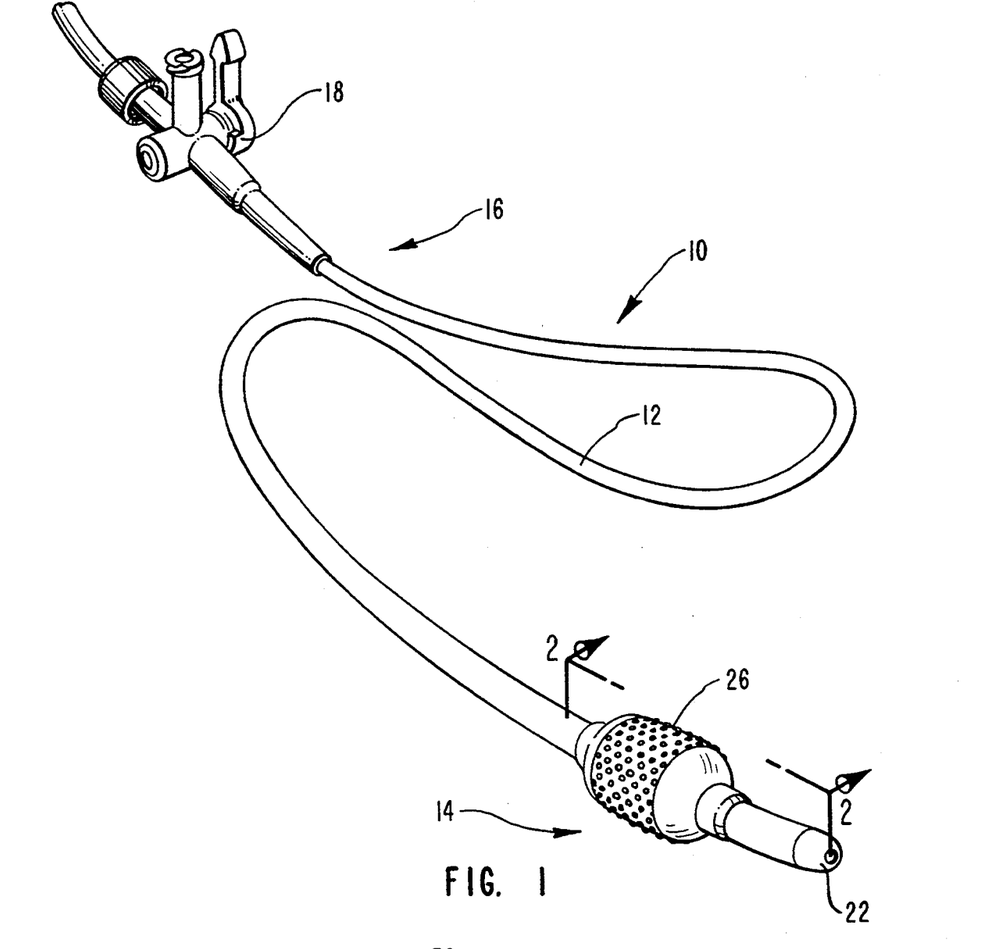
FIG. 1 is a perspective view of one presently preferred embodiment within the scope of the present invention.
Figure 2:
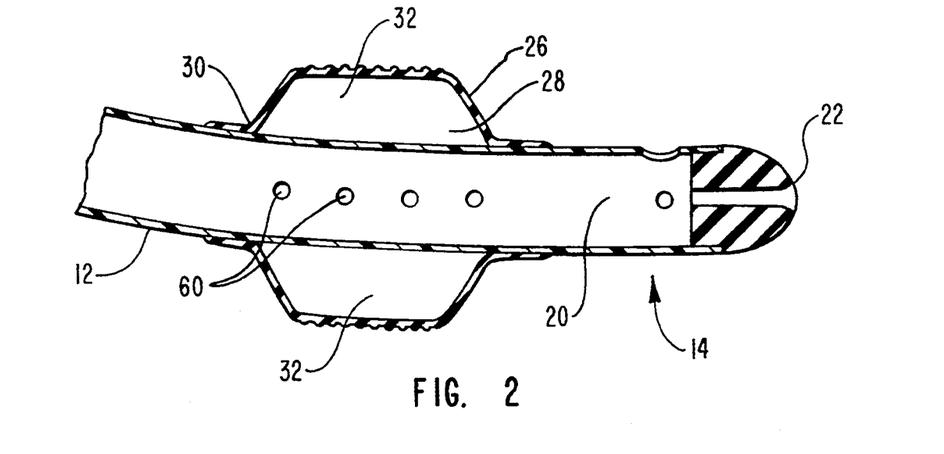
FIG. 2 is a cross-sectional view of the proximal end of the embodiment illustrated in FIG. 1, taken along line 2—2 of FIG. 1.

Reference is now made to the drawings wherein like parts are designated with like numerals throughout. Referring first to FIGS. 1 and 2, one presently preferred embodiment within the scope of the present invention is illustrated and generally designated 10. Catheter 10, as illustrated, is particularly designed for insertion into a body passageway so that a solution can be flowed therethrough.

The apparatus as illustrated in FIGS. 1 and 2 includes a flexible cannula 12 having a distal end 14, a proximal end 16, and at least one lumen 20. The distal end 14 is of a size which is capable of insertion into a patient's body passageway. A tip 22 is located at the end of distal end 14. The proximal end 16 is capable of connection to an outside location. A coupling device 18 for attaching the catheter to a solution source or to some external location is attached to the proximal end 16 of the cannula. When a solution source is coupled to the catheter, the solution may typically be provided through either a volumetric pump or a bag of solution within a pressure cuff. The solution may also be gravity fed. When fluid is being withdrawn from rather than infused into the body passageway, the catheter may be connected to a receiving vessel.

An inflatable balloon 26 is located near the distal end of flexible cannula 12, slightly proximal from tip 22. Balloon 26 comprises a distal end 28 and a proximal end 30, and forms an inner chamber 32 inside the balloon and outside flexible cannula 12. In one embodiment of the present invention, the distal end 28 of balloon 26 is located from approximately 2.0 cm to approximately 6.0 cm back from tip 22. Such an embodiment permits tip 22 to be inserted far into a body passageway, yet still permits balloon 26 to firmly engage the passageway. For most purposes, the distal end 28 of balloon 26 is preferably located from about 0.5 cm to about 4.0 cm back from tip 22.

Balloon 26 preferably has a cross-sectional diameter which is slightly larger than the cross-sectional diameter of the body passageway within which it is to be inserted. This is so that the balloon, when inflated, lodges firmly within the body passageway.

In one currently preferred embodiment of the present invention which is useful for infusing cardioplegia solution, the balloon has a cross-sectional diameter from about 1.7 cm to about 1.8 cm. Upon insertion within the body passageway, when the balloon has not been filled with cardioplegic solution, the balloon becomes slightly wrinkled about its outer periphery due to a small diameter of a body passageway. However, during infusion of the solution, the balloon is filled and becomes turgid in order to firmly engage the walls of the body passageway.

It will be appreciated that the body passageways of pediatric patients may be somewhat smaller than those of an adult patient. As a result, a catheter designed for pediatric use is necessarily designed so that the balloon has a smaller diameter adapted to fit within the smaller body passageways of the pediatric patient.

Once the catheter is placed within the body passageway and the balloon is inflated, the catheter is held in place by gripping means projecting from the outer surface of the balloon for securely gripping the walls of the body passageway to secure the catheter in place. A seal within the body passageway is also formed. This important gripping aspect of the present invention may comprise at least one irregularity in the outer surface of the balloon.

In the preferred embodiment, the gripping means comprises a plurality of protuberances that project outwardly from the outer surface of balloon 26. It will be appreciated that various configurations of protuberances will accomplish the teachings of the present invention. As used herein, the term "protuberance" refers to a projection from the outer surface of a balloon that assists in the retention of that balloon in a body passageway of a patient. The protuberances are soft enough to grip the walls of the body passageway without damaging the tissues. Examples of configurations satisfying the protuberances of the present invention are illustrated in FIGS. 5, 6, 7, and 8, and it will be appreciated that other configurations would also be useful.

Figure 5:
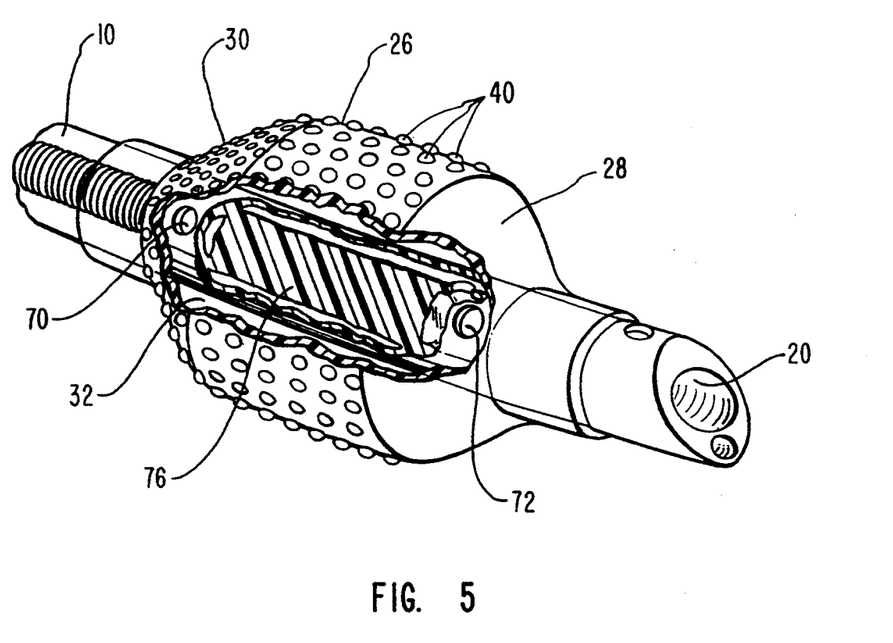
FIG. 5 is a broken-away perspective view of another embodiment of the inventive balloon catheter.

In the embodiment of the present invention shown in FIG. 5, the protuberances advantageously take the form of knobs 40 which serve to grip the walls of a body passageway during inflation of the balloon. Since some solutions and procedures such as normothermic cardioplegia tend to soften the material of which the balloon is constructed, knobs 40 provide a measure of safety by assuring that catheter 10 is not displaced during perfusion.

As can be seen in FIG. 5, knobs 40 preferably each have generally a cylindrical base formed in the outer surface of balloon 26, and a body which projects outwardly from the outer surface of the balloon and ends in a rounded terminus capable of gripping the inner wall of the body passageway when balloon 26 is inflated therein. The knobs 40 are soft enough so that they grip the walls of the passageway without damaging the tissues.

Knobs 40 may be formed on balloon 26 along the outer surfaces of the proximal end 30 and middle portions of balloon 26. Although not shown, knobs 40 may also be formed on the distal end 28 of the balloon 26. It is preferred, however, to have the distal end 28 be free from the knobs so that insertion of the catheter into the body passageway is not impeded. In the preferred embodiment, knobs 40 comprise a generally hemispherical shape. Knobs 40 also may comprise a conical shape, as well as other protruding shapes.

Figure 6:
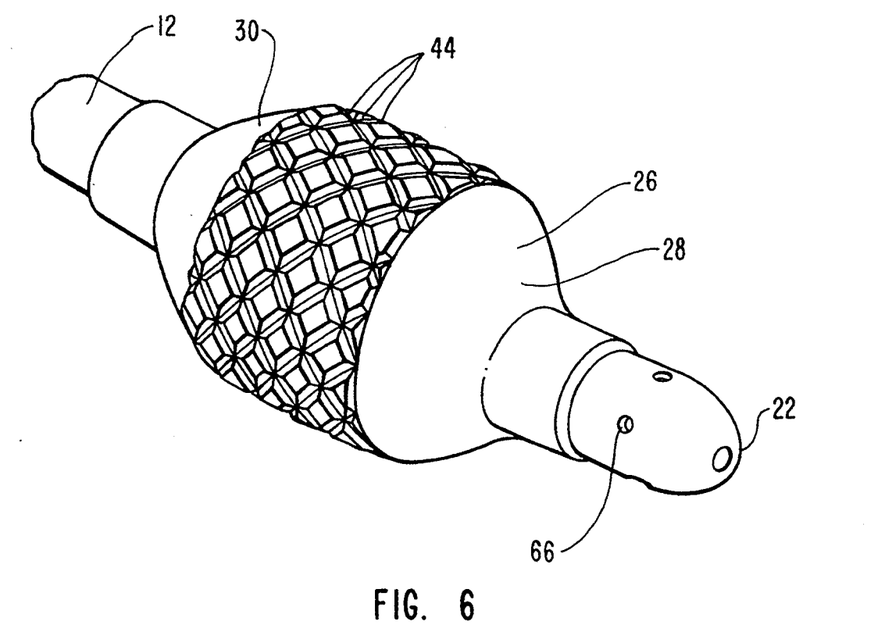
FIGS. 6, 7, and 8 are perspective views of presently preferred embodiments of balloons useful in the practice of the present invention.

FIG. 6 illustrates protuberances that take the form of a cross-hatched pattern 44 projecting outwardly from the exterior surface of balloon 26.

Figure 7:
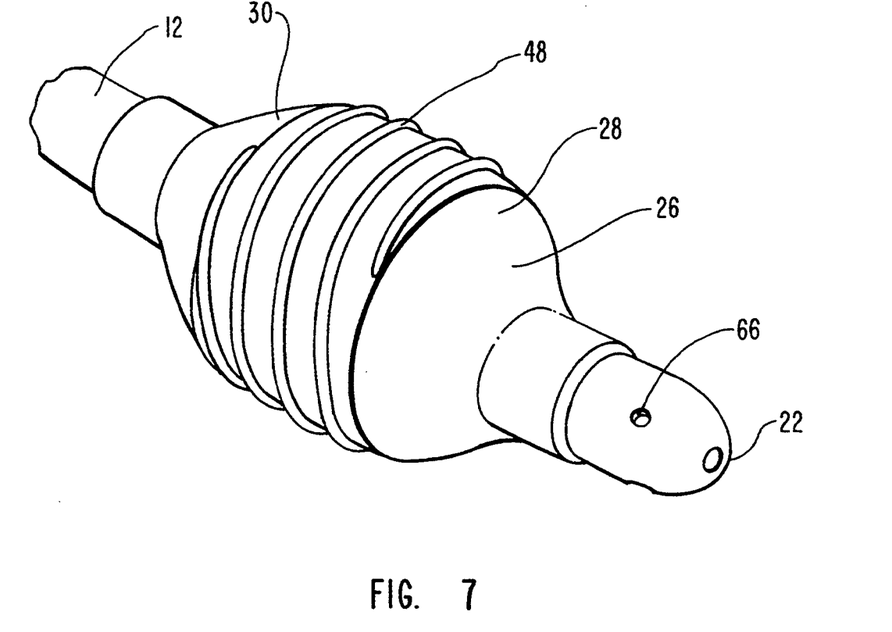

FIG. 7 illustrates protuberances in the form of an outwardly projecting spiral ridge 48 wound about the exterior surface of balloon 26. When inflated, the spiral ridge 48 contacts and tightly grips the walls of a body passageway in which it is inserted.

Figure 8:
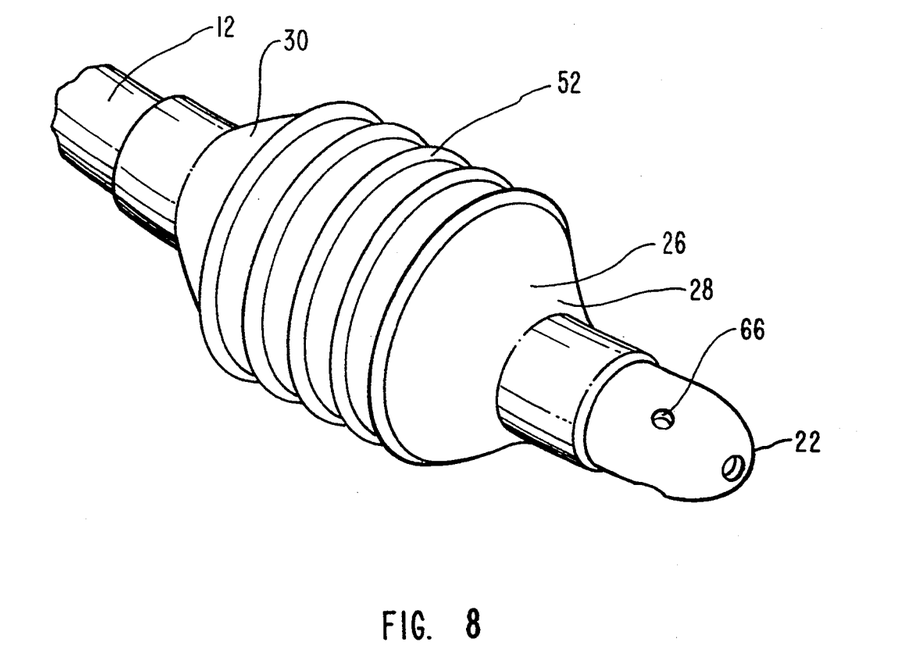

FIG. 8 illustrates yet another embodiment of the present invention, wherein the protuberances are in the form of outwardly projecting annular rings 52 wound about the exterior surface of balloon 26. As with the other embodiments, annular rings 52 assist in maintaining contact between an inflated balloon 26 and the walls of the body passageways.

It is also within the scope of the present invention for the gripping means to comprise at least one indentation projecting inwardly from the surface of the balloon. The at least one indentation forms an irregular shape on the outer surface of the balloon which secures the cannula in place by gripping the body passageway.

The balloon catheter of the present invention further comprises expansion means for inflating balloon 26. The expansion means communicate with the chamber 32 of balloon 26 such that air or fluid may pass therethrough in order to inflate the balloon. The type of expansion means preferred for use is dependent upon the type of balloon attached to the catheter. Balloon 26 may be either a self-inflating or a manually inflating balloon.

An example of a self-inflating balloon is illustrated in FIG. 2. The expansion means comprises at least one aperture 60 in lumen 20 of flexible cannula 12. Illustrated in FIG. 2 is a plurality of apertures 60 which present a cross area greater than the diameter of lumen 20, so that the chamber 32 within balloon 26 is more easily infused with fluid than is the body passageway into which the catheter is inserted. Hence, back pressure during infusion results in inflation of the balloon.

More specifically, apertures 60 are positioned on the lumen 20 at an area of the lumen which opens into the chamber 32 formed between balloon 26 and cannula 12. Fluid flowing through lumen 20 enters chamber 32 through apertures 60 and thereby inflates balloon 26. While fluid flows through the lumen 20, balloon 26 remains inflated. When the fluid flow is halted, the fluid drains out of balloon 26 and the balloon loses it turgidity. Once deflated, the seal is broken between the catheter and the body passageway, and the grip is released. The catheter can then be easily removed from the body.

As previously stated, when balloon 26 is inflated, the gripping means on the exterior of the balloon contact and grip the walls of the body passageway. Thus, while fluid is being infused or withdrawn, the balloon will remain inflated and securely positioned.

The total cross-sectional area of balloon apertures 60 is preferably in the range from approximately 1.0 to approximately 5.0 times the cross-sectional area of lumen 20 in order to facilitate rapid filling and emptying of balloon 26. In the presently preferred embodiment within the scope of the present invention, the total cross-sectional area of balloon apertures 60 is about 1 to 2 times the cross-sectional area of lumen 20.

The embodiment illustrated in FIGS. 1 and 2 shows four balloon apertures 60. In practice, the number of openings is dependent on various factors. On one hand, the total cross-sectional area of the apertures must be large (relative to the cross-sectional area of the lumen) in order for the balloon to be self-filling. On the other hand, too many apertures or too large or improperly configured apertures can compromise the structural integrity of the catheter, thereby causing the tube to bend and/or collapse during use and inhibit flow of solution through the catheter.

Thus, there is a balance between having enough properly shaped and sized openings to create a large total cross-sectional area and having too many openings which weaken the catheter. Hence, while more or fewer apertures can be readily made to work, eight apertures, in two pairs of four each, have been found to be satisfactory for most situations.

In one balloon catheter within the scope of the present invention, at least one lumen outlet 66 may be located on lumen 20 between balloon 26 and rounded tip 22. Lumen outlet 66 allows the solution to exit catheter 10 and enter the body of the patient.

In some instances, low flow rates and pressures are necessary. For example, normothermic cardioplegia is a semi-continuous process requiring lower flow rates and pressures than intermittent hypothermic cardioplegia. Thus, it has been found that the total cross-sectional area of the least one lumen outlet 66 should be less than the cross-sectional diameter of balloon apertures 60.

In the presently preferred embodiments, there are provided a multiple of lumen outlets 66. The total cross-sectional area of lumen outlets 66 is in the range from about fifteen percent (15%) to about fifty percent (50%) of the cross-sectional area of lumen 20. The presently preferred total cross-sectional area of lumen outlets 66 is approximately thirty-five percent (35%) of the cross-sectional area of lumen 20. It should be appreciated that the number of lumen outlets is variable, and the present invention is not limited to a particular number of lumen outlets.

When determining size of lumen outlets 66, care should be taken so that the lumen outlets are not so small that the solution exits the catheter in a jet-like flow which could harm the body passageways. To further reduce any potential trauma to the body passageway from the exiting solution, the lumen outlets are preferably bored in the lumen at an angle so that the solution exits the catheter in a forward direction.

Because the total cross-sectional area of balloon aperture 60 is preferably substantially greater than the total cross-sectional area of lumen outlets 66, the fluid pressure of flowing solution within the balloon chamber 32 is greater than the fluid pressure at the point the solution exits the catheter. In this way, the self-filling balloon automatically fills as solution flows through the lumen. When the solution flow stops, the balloon empties as the solution drains into the body passageway.

FIG. 5 illustrates an embodiment of the present invention that utilizes two larger balloon apertures, proximal balloon aperture 70 and distal balloon aperture 72. Solution passing through lumen 20 must enter inner chamber 32 of balloon 26 through proximal balloon aperture 70. The passage of solution inflates balloon 26, wedging it into the body passageway. After balloon 26 becomes turgid, the solution exits inner chamber 32 through distal balloon aperture 72. Lumen 20 is blocked by an internal plug 76 located between proximal balloon aperture 70 and distal balloon aperture 72.

Figure 3:
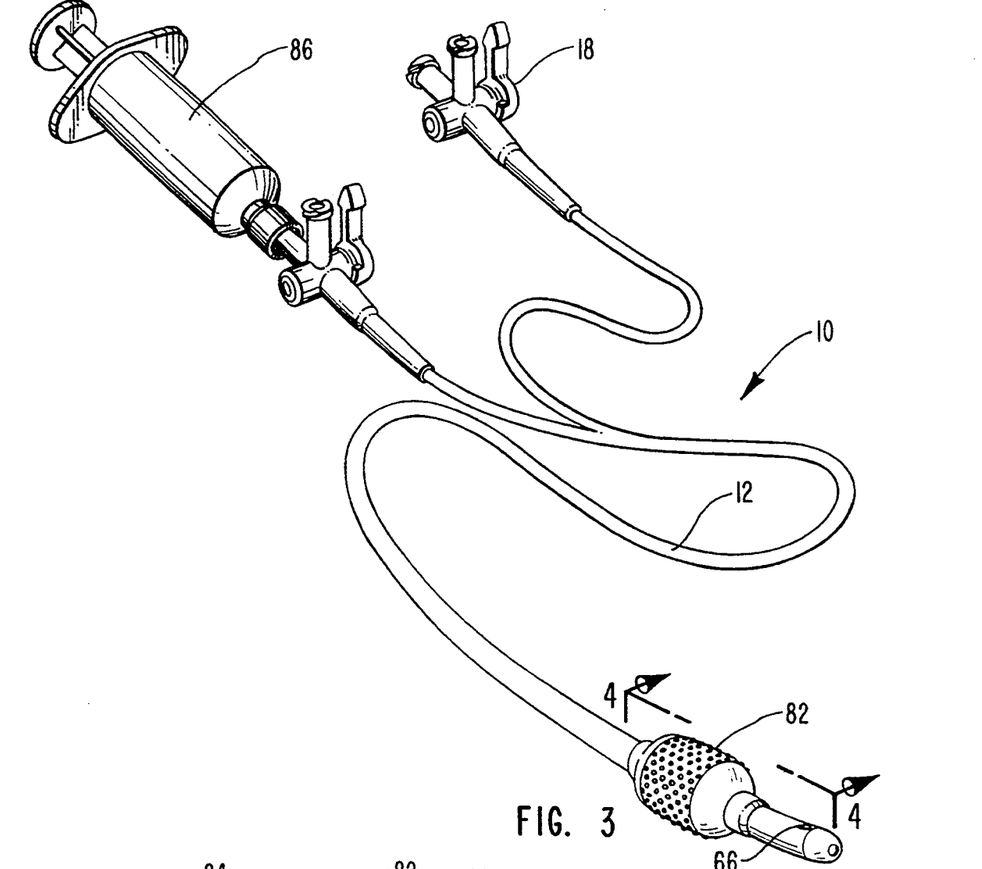
FIG. 3 is a perspective view of a manually inflated balloon catheter.
Figure 4:
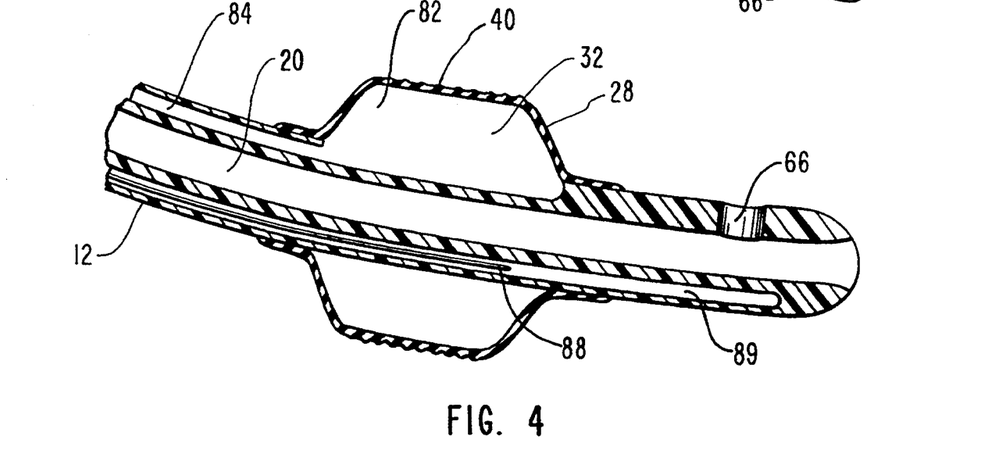
FIG. 4 is a cross-sectional view of the distal end of the manually inflatable balloon catheter illustrated in FIG. 3, taken along line 4—4 of FIG. 3.

A second type of balloon within the scope of the present invention is a manually inflatable balloon 82 as illustrated in FIGS. 3 and 4. With a manually inflatable balloon, the balloon does not automatically inflate when a solution flows through the catheter. This can be an advantage at times when the flow of solution into a body passageway is needed only intermittently rather than continuously. During periods of time when no solution is needed, the catheter will still be held firmly in place.

In contrast, a self-inflated balloon would be secure only when solution is flowed through the catheter. During periods of non-use, the balloon would be deflated, and the catheter would no longer be lodged in place. The catheter would then be able to move freely within the body passageway, thus moving away from the desired position and possibly causing damage or irritation to the tissues.

As illustrated in FIG. 4, the expansion means for the manually inflatable balloon 82 comprises an inflation lumen 84 which is separate from the main lumen 20 and which is in communication with the balloon 82. Through inflation lumen 84 air or fluid may be passed into the balloon in order to fill and inflate the balloon.

Specifically, inflation lumen 84 opens at one end into the chamber 32 of balloon 82 and is connectable at the opposite end to an inflation source. As shown in FIGS. 3 and 4, in order to inflate balloon 82, the material of the inflation source is pushed through inflation lumen 84 and into balloon 82 by an inflator 86 connected to the catheter at its distal end 16. Once balloon 82 is inflated, the plurality of protuberances on the balloon contacts the walls of the body and holds the catheter firmly within the body without excess movement of the catheter. When deflation is desired, the inflator 86 can be used to withdraw the gas or fluid and therefore deflate the balloon.

As seen in FIG. 3, one presently preferred inflator 86 is a syringe. However, other ways of pushing the material through the inflation lumen are also within the scope of the present invention. For example, a pump may be connected to the inflation lumen to pump gas or fluid therethrough. Another alternative would be to connect a rubber bulb to the end of the inflation lumen so that pressure on the rubber bulb would force gas or fluid through the lumen. The solution may also be gravity fed through the catheter.

The balloons of the present invention can be attached to the catheter 10 in many ways. One preferred method of attaching the balloon to the flexible cannula is solvent bonding with tetrahydrofuran, though other solvents such as silicone paste, dimethylformamide ("DMF"), acetone, and cyclohexanone, for example, could be substituted. The balloon is attached to the flexible cannula according to techniques well-known in the art. The flexible cannula may be assembled using an RTV silicone paste that is cured with ultraviolet light to form a bond with the balloon.

The flexible cannula is preferably constructed of a material which retains its flexibility after prolonged exposure to temperatures of at least about 0° C. It is currently preferred that the cannula be constructed of medical-grade polyvinyl chloride, having a softness of about 75 to 85 durometer Shore-A. Other suitable materials may also be used to construct the flexible cannula, such as medical-grade silicone and polyurethane.

It is important that the flexible cannula not only be flexible enough to be manipulated and positioned within a body passageway, but also that it have sufficient rigidity and structural integrity so as to not collapse or bend during use. In addition, the flexible cannula should be soft enough to compress or deflect when pressed against the body passageway so as to protect the body passageway from inadvertent puncture, but not so soft that a suture tie holding it in place occludes the cannula.

Reference is now made to the distal end 14 of the cannula as illustrated in FIG. 2. In the preferred embodiment of FIG. 2, distal end 14 may be comprised of a soft rounded tip 22 which is preferably constructed of a material which will minimize the trauma and the risk of causing damage to the body passageway during insertion and use. However, an angled, or other shaped tip, as illustrated in FIG. 5, is also within the scope of the present invention.

The rounded tip of distal end 14 is preferably constructed of medical-grade silicone, having a softness of about 55 to 65 durometer Shore-A. Other suitable materials such as polyvinyl chloride, polyurethane, or other thermoplastic elastomers and plasticized thermoplastics may also be used to construct the rounded tip.

In the presently preferred embodiment of the present invention as illustrated in FIG. 2, balloon 26, when inflated, tapers at its proximal end 30 and at its distal end 28. The balloon increases in diameter from proximal end 30 of the balloon 26 to the full diameter of a cylinder, and then tapers inwardly at distal end 28 of balloon 26. The structure of the taper allows solution to be infused into the more proximal branches of the body passageways, thereby providing thorough flow of solution.

If the taper is too abrupt, the balloon may be difficult to properly insert and position within the body passageway, and there may be more likelihood of trauma to the tissues as the cannula is inserted and positioned. If the taper is too gradual, the balloon may be too long to fit within the body passageway and still engage the walls.

The balloons of most balloon catheters known in the art expand and collapse depending upon the fluid pressure within the balloon compared with the fluid pressure outside the balloon. It has been found that the pressure required to inflate conventional balloon catheters to seal the body passageway often results in an excessive infusion pressure (e.g. greater than 50 mm Hg) that may cause barotrauma. The low-operating fluid pressures used in connection with the present invention could not adequately inflate conventional balloon catheters and thereby provide a safer inflation pressure that would minimize barotrauma to the body passageway.

In response to this problem, the self-filling balloon of the present invention is constructed so that it is not necessary for the balloon to expand significantly from its unfilled state in order to seal the body passageways. Thus, upon filling, the balloon becomes turgid, but not significantly distended beyond the balloon's original shape.

Another important aspect of the present invention as shown in FIG. 4, is a malleable wire 88 which may be placed within the cannula of the balloon catheter to assist in maintaining the shape of cannula 12 after insertion into the body passageway. As seen in FIG. 4, the wire 88 is placed in contact with the wall of the catheter and may terminate approximately at the distal end 28 of the balloon 82. By stopping the wire 88 before the end of the balloon, the design protects against possible trauma to the heart or other body tissues. The malleable wire 88 may be placed anywhere along the length of the cannula where support is desired. It is preferred that the malleable wire run along the catheter to the point of insertion of the catheter into the body, thereby supporting and stiffening the portion of the catheter located at the point of insertion.

In one embodiment within the scope of the present invention, the catheter may comprise a separate malleable wire lumen 89 to house malleable wire 88. Although malleable wire is pictured in FIG. 4 with a catheter having thereon a manually inflatable balloon 82, it can be appreciated that malleable wire 88 can be utilized with a self-inflatable catheter as well.

Some solutions such as normothermic cardioplegia causes most catheter materials to become soft. As a result, the catheters may become too soft to retain its place within the body passageways during infusion of the softening solutions. One solution could be to produce a catheter of a material stiff enough to retain the shape of the catheter under normothermic conditions. However, a catheter of this hard material could injure the sensitive tissues of the body during insertion and use. Therefore, positioning of a malleable wire within the cannula in order to stiffen and support the cannula, or various portions of the catheter, is an important advantage. Malleable wire 88 allows a soft catheter material to be used, while insuring that the shape of the catheter is maintained during use within the body passageway.

Figure 9:
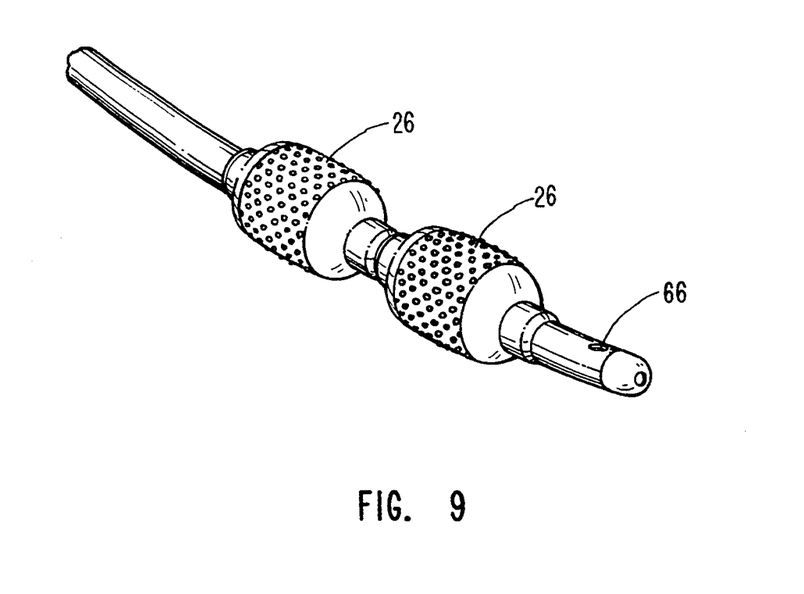
FIG. 9 is a perspective view of a double balloon catheter.

Various types of catheters other than those already discussed may also be used with the balloon of the present invention. For example, the balloon, whether self or manually inflated, may be used with double balloon catheters. With double balloon catheter, as the name implies, more than one balloon is located on the catheter. A double balloon catheter is illustrated in FIG. 9. Having two balloons located on the catheter allows separation of the sealing and gripping functions of the catheter. One balloon may be used for sealing the body passageway, while the second balloon may be used for securing the catheter in place within the body passageway.

The balloon used for securing may comprise at least one irregularity on the surface of the balloon which tightly and securely grips the walls of the body passageway when the balloon is inflated. The at least one irregularity may comprise a plurality of protuberances projecting outwardly from the outer surface of the balloon. The at least one irregularity may also comprise at least one indentation projecting inwardly from the surface of the balloon.

The sizes of the balloons may differ with different sizes of passageways. Although FIG. 9 illustrates a double catheter balloon wherein both balloons are of the same size, it can be appreciated that many different size combinations are possible. For passageways of uniform diameter, the diameters of the balloons may be the same, but the lengths may differ. For example, it can be appreciated that the sealing balloon may be a shorter balloon than the gripping balloon. The gripping balloon may be longer so as to be able to grip a larger surface area of the body passageway.

For passageways wherein an area of the passageway is more narrow than a second area, the balloons may be sized so as to fit comfortably within each respective area.

In a preferred embodiment, the more proximal balloon is larger than the more distal balloon and serves to retain the catheter in place. The more distal balloon is smaller and serves to form a seal between the catheter and the body passageway.

It can be appreciated that various combinations of lengths, diameters, and gripping means may be used for the inflatable balloons of the double ballooned catheters within the scope of the present invention. The important aspect is that the sealing and gripping functions of the catheter can be separated by using at least two balloons within the catheter.

Another type of catheter which may be used with the balloon of the present invention is one which can be used for retrograde or antegrade venous administration of cardioplegic solutions.

Typically, this type of catheter contains more than one lumen. The main lumen passes the solution to the body. Other lumens perform such function as temperature and pressure sensing. For example, a sensing lumen orifice near the distal end of a pressure-sensing lumen permits sensing of fluid pressure at the point where the cardioplegic solution exits the catheter within the coronary sinus. It is important to closely monitor the pressure within the coronary sinus, because if the fluid pressure exceeds a predetermined maximum pressure (as discussed in greater detail hereinafter), tissue damage and edema to the coronary sinus and other heart tissues will likely result.

The cross-sectional area of a sensing lumen orifice is equal to or greater than the cross-sectional area of a pressure-sensing lumen. In one presently preferred embodiment, the cross-sectional area of a sensing lumen orifice is in the range from about 2 to about 3 times the cross-sectional area of a pressure-sensing lumen.

A means for receiving sensed pressure of the cardioplegic solution may be provided by a pressure-sensing feed line, which is an extension of the pressure-sensing lumen. The pressure-sensing feed line may branch from flexible cannula 12 near the proximal end of the catheter.

It will be appreciated that a pressure-sensing feed line may also consist of an optical fiber for transmitting sensed information from a pressure-sensing lumen orifice. A three-way stopcock may be located at the proximal end of the pressure-sensing feed line. The three-way stopcock permits coupling to a pressure-sensing device at one setting, removing air from the pressure-sensing lumen at a second setting, and sealing the feed line at the third setting. The pressure-sensing lumen is occluded at a point proximal to the point that the feed line branches from the flexible cannula to prevent introduction of cardioplegic solution into the pressure-sensing lumen.

A temperature sensing lumen may also be provided with a means attached to the proximal end of the temperature-sensing lumen for receiving the sensed temperature of the cardioplegic solution. The means for receiving the sensed temperature may comprises a temperature-sensing thermistor capable of sensing the temperature of the cardioplegia solution as it is infused into the coronary sinus. The thermistor is in communication with the cardioplegic solution through a temperature-sensing orifice.

During the administration of cardioplegia, it is also desirable to monitor several chemical and physical properties of the infused cardioplegic solution. Factors such as pressure, temperature, pH, and the partial pressure of oxygen indicate the condition of the cardioplegic solution. External monitoring has proven unsatisfactory as the attributes of the cardioplegic solution often;-change during passage through the catheter.

This problem can be solved by providing sensing devices located at the tip of the catheter to provide real-time measurements of cardioplegic solution characteristics. It will be appreciated, therefore, that it is within the scope of the present invention to use the balloons with catheters having a lumen to house other sensing devices such as a pH sensor, oxygen sensor or an optical fiber.

The balloon of the present invention can also be used with additional sensing devices combined in catheters with more than three lumens.

B. Methods of Using the Balloon Catheter

Figure 10:
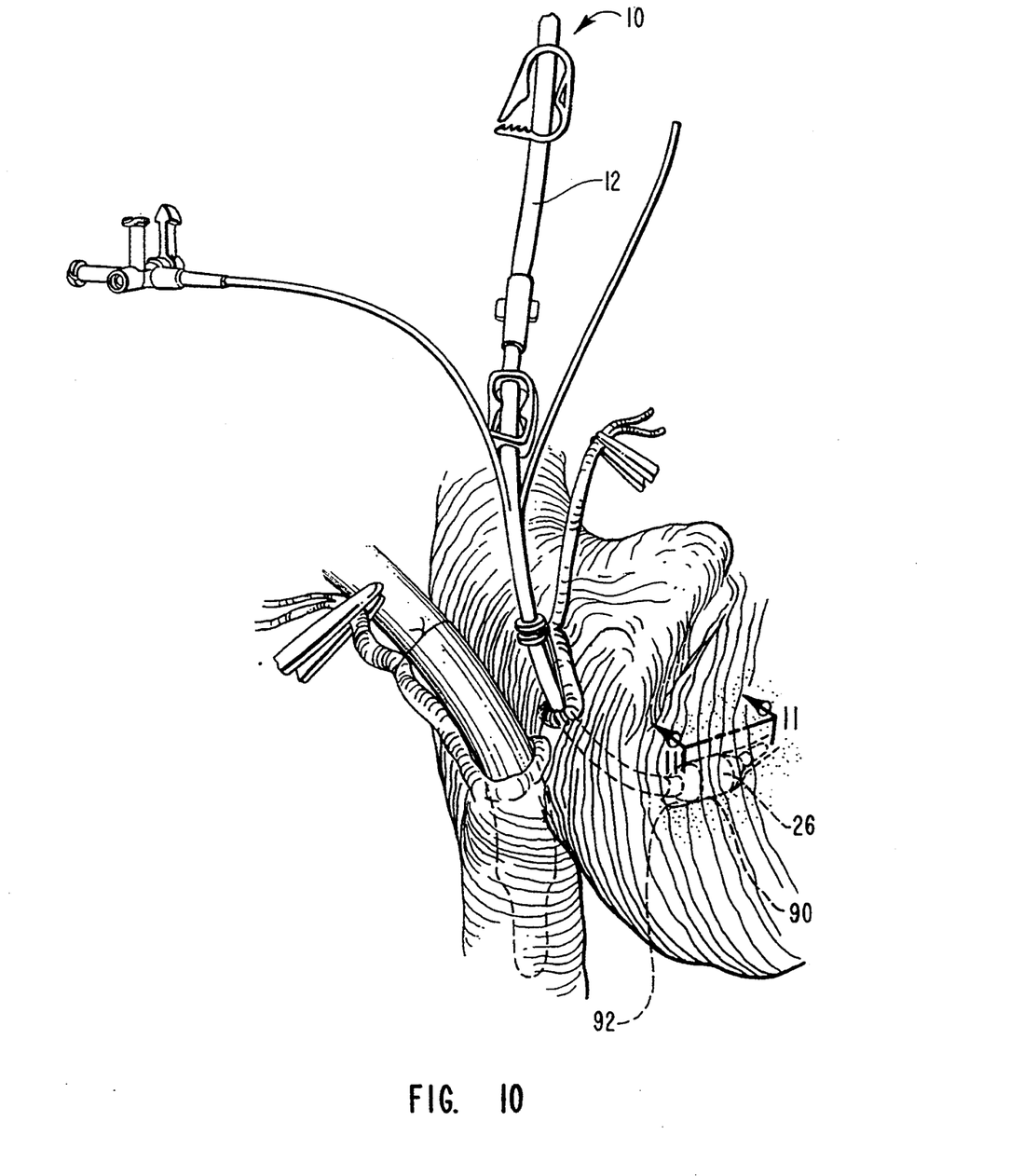
FIG. 10 is a perspective view illustrating a preferred embodiment of the balloon catheter of the present invention, when inserted within the coronary sinus of the heart for use in retrograde cardioplegia.

Referring now to FIG. 10, catheter 10 is shown inserted into a body passageway. By way of example, the catheter 10 has been inserted into a small incision which has been made within the confines of a mattress suture placed in the right atrium. The incision is preferably less than one centimeter long and is from about one inch to about two inches from the entrance of the coronary sinus. A purse-string suture is placed to seal the right atrium incision around the catheter.

Because the right atrium is not completely opened by the methods of the present invention, it is not necessary to isolate the right heart by tying and cannulating both venae cavae. This not only simplifies the surgical procedure, but also reduces the trauma experienced by the patient. In addition, because the incision in the right atrium is very small, there is little risk that the patient will develop a heart arrhythmia which often occurs when the right atrium is opened.

Conventional cardioplegic solutions known in the art may be used in performing retrograde cardioplegia within the scope of the present invention. The same cardioplegic solution source used for performing retrograde cardioplegia may be used for performing both retrograde and antegrade cardioplegia.

Figure 11:
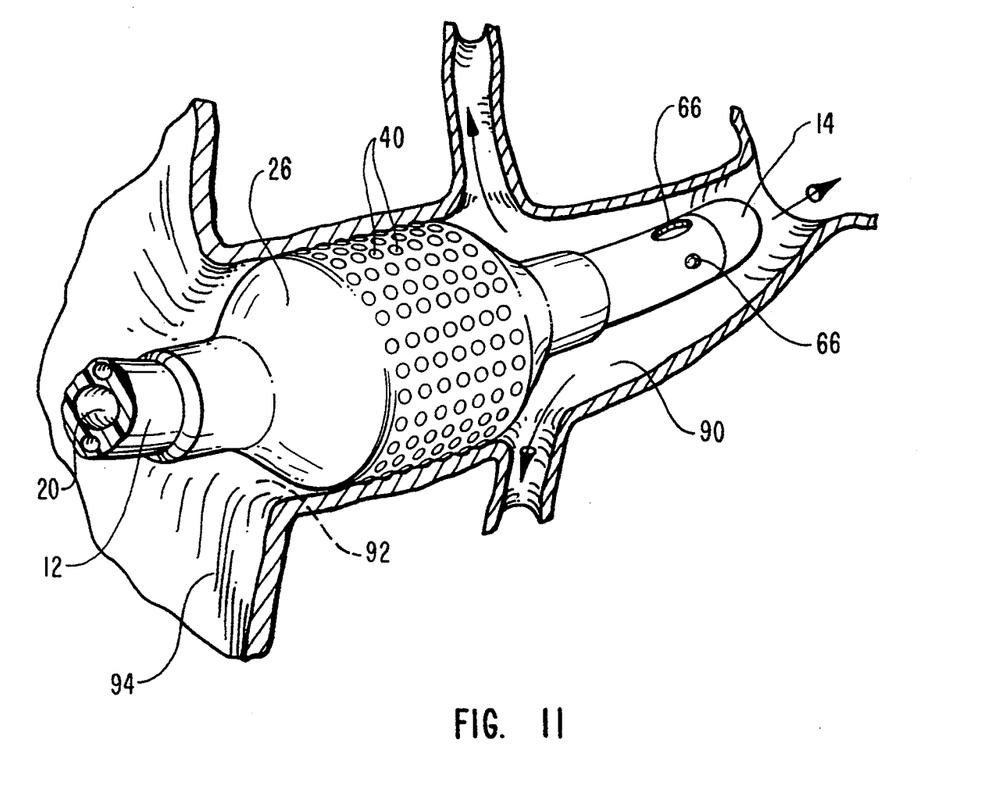
FIG. 11 is a partial cross-sectional perspective view of the retrograde cardioplegic catheter within the coronary sinus taken along line 11—11 of FIG. 10.

FIGS. 10 and 11 illustrates placement of catheter 10 within coronary sinus 90. As seen in FIG. 11, balloon 26 is positioned just within coronary sinus orifice 92 of right atrial wall 94. As the solution flows through lumen 20, the fluid flows through the balloon apertures to fill balloon 26. Upon filling, the self-filling balloon becomes turgid but not significantly distended beyond its original shape.

Once infusion of the cardioplegic solution stops, the balloon empties to allow normal antegrade flow into the right atrium. The catheter does not need to be removed to allow for normal antegrade flow.

It has been found that if the pressure within the body passageway exceeds about 60 mm Hg, venular damage and hemorrhage may result. It will be appreciated that this maximum pressure may vary from patient to patient, but this pressure is a conservative maximum pressure. Therefore, the pressure within the body passageway is preferably maintained below approximately 50 mm Hg in order to provide a margin of error. The pressure within the inner chamber of the self-filling balloon will be somewhat greater than the pressure within the body passageway due to the pressure drop associated with the lumen outlets. Since excessive pressure within the balloon may cause the balloon to expand and injure the body passageway, the pressure within the balloon is preferably maintained below about 150 mm Hg.

Because of the pressure drop through the lumen and associated connectors, the pressure within the self-filling balloon is less than the system pressure at the cardioplegic solution source. If the cardioplegic solution contains blood, then care should be taken to maintain the source pressure below approximately 300 mm Hg. This is because it has been found that blood subjected to pressures exceeding about 300 mm Hg is subject to hemolysis.

The cardioplegic solution flow rate should be adjusted to maintain a safe pressure within the body passageway, within the inner chamber of the self-filling balloon, and throughout the cardioplegia system. The flow rate is preferably maximized within the above constraints.

Under anticipated operating conditions, the flow rate of cardioplegic solution will be preferably in the range from about 50 ml/min to about 150 ml/min. The flow rate may vary depending upon the extent of coronary obstructions within the patient's heart and upon other heart conditions, such as heart temperature and muscular tone of the coronary circulatory system. Because the catheter is securely positioned within the coronary sinus during the entire surgical procedure, there is no need to repeatedly insert the catheter within the body passageway or to hand hold the catheter during infusion.

During lengthy cardiac surgery, continuous infusion of the cardioplegic solution provides a number of significant benefits. For example, continuous infusion (1) maintains arrest, (2) restores desired levels of nutrients, (3) buffers acidosis, (4) washes acid metabolites away which inhibit continued anaerobiosis, (5) replenishes high-energy phosphates if the cardioplegia solution is oxygenated, (6) restores substrates depleted during ischemia, and (7) counteracts edema.

The present invention is particularly useful in delivering retrograde venous cardioplegia in combination with antegrade cardioplegia. A combination of retrograde and antegrade cardioplegia provides more homogeneous distribution of the cardioplegic solution to the right and left ventricles, stops the heart faster, and leads to more complete regional recovery of the jeopardized muscle and the global left and right ventricles as compared to the use of antegrade cardioplegia alone. When using a manually inflatable balloon catheter, the method would further comprise activating the inflator in order to inflate the textured balloon.

From the foregoing, it will be appreciated that the present invention provides apparatus and methods for using and manufacturing a textured balloon catheter for infusing a solution into a body passageway, whereby the catheter is held securely within the passageway by a plurality of protuberances projecting outwardly from the exterior of the balloon.

Additionally, it will be appreciated that the present invention further provides apparatus and methods for infusing a solution such as cardioplegia into the body for use in performing retrograde cardioplegia where right atrial isolation, right atriotomy, and repeated cannulation of the apparatus are not required.

Likewise, it will be appreciated that because the present invention provides a textured balloon catheter which can be quickly and accurately inserted within the body passageway, the patient suffers relatively little trauma.

It will also be appreciated that the present invention provides apparatus and methods for infusing a solution into a body passageway whereby the textured balloon catheter retains its shape while within the body.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A balloon catheter for use in transporting a fluid between an external location and a body passageway comprising:
   a. a flexible cannula having at least one lumen, the flexible cannula having a distal end being of a size capable of insertion into a body passageway, and a proximal end capable of connection to an outside location, said cannula being adapted to transport fluids between the outside location and the body passageway when inserted therein;
   b. a balloon, having a distal end and a proximal end, attached to the cannula periphery near the distal end of said cannula, thereby forming a chamber within the balloon and outside of the cannula;
   c. expansion means in communication with the balloon for admitting fluid into and thereby inflating said balloon; and
   d. knob means for securely gripping the walls of the body passageway when the balloon is inflated in order to secure the catheter in place during use and forming a seal within the body passageway, said knob means comprising a plurality of knobs projecting outwardly from the outer surface of said balloon, and wherein the plurality of knobs are formed from a material and are of a size and shape that they will securely grip the walls of a body passageway and form a seal within the body passageway when the balloon is inflated.

2. A balloon catheter as defined in claim 1, wherein the expansion means comprises an inflation lumen in communication with the balloon, for use in inflating the balloon.

3. A balloon catheter as defined in claim 1, wherein the expansion means comprises at least one aperture in the at least one lumen of the flexible cannula, such that fluid flowing through the lumen will flow through the at least one aperture into the interior of the balloon, thereby inflating the balloon.

4. A balloon catheter as defined in claim 3, further comprising an internal plug positioned within a lumen, thereby blocking passage through said lumen.

5. A balloon catheter as defined in claim 4, wherein the at least one aperture comprises a distal balloon aperture located on the lumen distal to the internal plug and a proximal balloon aperture located on the lumen proximal to the internal plug, such that fluid flowing through the lumen will exit the lumen at the distal balloon aperture and enter the balloon chamber, thereby filling the balloon, and will exit the chamber and re-enter the lumen through the proximal balloon aperture.

6. A balloon catheter as defined in claim 1, wherein the plurality of knobs each has generally a cylindrical base formed in the outer surface of the balloon, a body which projects outwardly substantially perpendicularly from the outer surface of the balloon, and a rounded terminus capable of gripping the inner wall of the body passageway.

7. A balloon catheter as defined in claim 1, further comprising a malleable wire located within a portion of the cannula, the malleable wire being constructed of a malleable material such that the malleable wire can be used to assist in maintaining the shape of the flexible cannula in the body passageway, wherein the malleable wire extends within the cannula from the proximal end of the cannula to substantially near but not past the distal end of the balloon.

8. A balloon catheter as defined in claim 1, wherein the catheter further comprises a malleable wire lumen in which is positioned a malleable wire, the malleable wire being used to maintain the shape of the flexible cannula in the body passageway.

9. A balloon catheter as defined in claim 1, wherein said balloon is substantially cylindrical when inflated.

10. A balloon catheter as defined in claim 9, wherein the distal end of said balloon is tapered.

11. A balloon catheter as defined in claim 10, wherein the tapered distal end of the balloon is free of knobs.

12. A method for transporting a solution between an external location and a body passageway comprising the steps of:
   a. inserting a balloon catheter through a small incision or opening in the body into a body passageway, the catheter comprising:
      (1) a cannula having at least one lumen, the cannula having a distal end being of a size capable of insertion into a body passageway, and a proximal end capable of connection to an outside location;
      (2) a balloon attached to the cannula periphery near the distal end of the cannula, thereby forming a chamber within the balloon and outside of the cannula;
      (3) expansion means in communication with the balloon for admitting fluid into and thereby inflating said balloon; and
      (4) knob means for securely gripping the walls of the body passageway when the balloon is inflated so as to secure the cannula in place during use and forming a seal within the body passageway, the knob means comprising a plurality of knobs projecting outwardly from the outer surface of the balloon, and wherein the plurality of knobs are formed from a material and are of a size and shape that they will securely grip the walls of a body passageway and form a seal within the body passageway when the balloon is inflated;

b. introducing fluid through the expansion means so as to inflate the balloon, thereby allowing the knob means to securely engage the walls of the body passageway and form a seal therewith; and c. allowing solution to flow through the secured catheter.

13. A method as defined in claim 12, wherein the expansion means comprises an inflation lumen in communication with the balloon, for use in inflating the balloon.

14. A method as defined in claim 12, wherein the expansion means comprises at least one aperture in an area of the cannula within the chamber.

15. A method as defined in claim 12, wherein the catheter further comprises a malleable wire extending within the cannula from the proximal end to substantially near but not past the distal end of the balloon, the malleable wire being constructed of a malleable material such that the malleable wire can be used to assist in maintaining the shape of the flexible cannula in the body passageway.

16. A method as defined in claim 12, wherein the balloon is substantially cylindrical when inflated.

17. A method as defined in claim 16, wherein the distal end of said balloon is tapered.

18. A method as defined in claim 17, wherein the tapered distal end of the balloon is free of knobs.

19. A balloon catheter for use in transporting a fluid between an external location and a body passageway comprising:

a. a flexible cannula having at least one lumen, the flexible cannula having a distal end being of a size capable of insertion into a body passageway, and a proximal end capable of connection to an outside location, said cannula being adapted to transport fluids between the outside location and the body passageway when inserted therein;

b. a balloon, having a distal end and a proximal end, attached to the cannula periphery near the distal end of said cannula, thereby forming a chamber within the balloon and outside of the cannula;

c. expansion means in communication with the balloon for admitting fluid into and thereby inflating said balloon; and d. a malleable wire located within a portion of the cannula, the malleable wire being constructed of a malleable material such that the malleable wire can be used to assist in maintaining the shape of the flexible cannula in the body passageway, wherein the malleable wire extends within the cannula from the proximal end of the cannula to substantially near but not past the distal end of the balloon.

20. A method for transporting a solution between an external location and a body passageway comprising the steps of:

a. inserting a balloon catheter through a small incision or opening in the body into a body passageway, the catheter comprising:

(1) a cannula having at least one lumen, the cannula having a distal end being of a size capable of insertion into a body passageway, and a proximal end capable of connection to an outside location;

(2) a balloon attached to the cannula periphery near the distal end of the cannula, thereby forming a chamber within the balloon and outside of the cannula;

(3) expansion means in communication with the balloon for admitting fluid into and thereby inflating said balloon; and (4) a malleable wire extending within the cannula from the proximal end to substantially near but not past the distal end of the balloon, the malleable wire being constructed of a malleable material such that the malleable wire can be used to assist in maintaining the shape of the flexible cannula in the body passageway;

b. introducing fluid through the expansion means so as to inflate the balloon; and c. allowing solution to flow through the secured catheter.

* * * * *